(12) United States Patent
Masyk

(10) Patent No.: US 10,888,632 B2
(45) Date of Patent: Jan. 12, 2021

(54) ULTRAVIOLET SANITATIONS SYSTEM AND METHOD

(71) Applicant: Mitchell James Masyk, Edmonton (CA)

(72) Inventor: Mitchell James Masyk, Edmonton (CA)

(*) Notice: Subject to any disclaimer, the term of this patent is extended or adjusted under 35 U.S.C. 154(b) by 0 days.

(21) Appl. No.: 15/722,714

(22) Filed: Oct. 2, 2017

(65) Prior Publication Data

US 2019/0192705 A1    Jun. 27, 2019

(51) Int. Cl.
| | | |
|---|---|---|
| *A61L 2/10* | (2006.01) | |
| *A47K 10/02* | (2006.01) | |
| *A61L 2/18* | (2006.01) | |
| *A47K 10/04* | (2006.01) | |

(52) U.S. Cl.
CPC ............... *A61L 2/10* (2013.01); *A47K 10/02* (2013.01); *A61L 2/18* (2013.01); *A47K 10/04* (2013.01); *A61L 2202/11* (2013.01); *A61L 2202/26* (2013.01)

(58) Field of Classification Search
CPC .. A61L 2/10; A61L 2/18; A47K 10/02; A47K 10/04
See application file for complete search history.

(56) References Cited

U.S. PATENT DOCUMENTS

| | | | |
|---|---|---|---|
| 4,182,050 A | 1/1980 | Righi | |
| 5,664,340 A | 9/1997 | Brown | |
| 6,565,819 B1 * | 5/2003 | Herrera | A46B 17/06 422/26 |
| 6,877,248 B1 | 4/2005 | Cross et al. | |
| 8,276,290 B2 | 10/2012 | Uhara et al. | |
| 8,881,422 B2 | 11/2014 | Abramovich et al. | |
| 2006/0242788 A1 | 11/2006 | Day | |
| 2008/0135061 A1 | 6/2008 | Madgar | |
| 2012/0042914 A1 | 2/2012 | Celotto et al. | |
| 2012/0056102 A1 * | 3/2012 | Stanley | G01J 1/0271 250/455.11 |
| 2013/0047345 A1 * | 2/2013 | Fast | C11D 3/39 8/137 |

FOREIGN PATENT DOCUMENTS

| | | |
|---|---|---|
| CN | 2564161 | 8/2003 |
| EP | 1696071 A1 | 8/2006 |

OTHER PUBLICATIONS

Hill (2010) (Year: 2010).*

* cited by examiner

*Primary Examiner* — Sean E Conley
*Assistant Examiner* — Brendan A Hensel
(74) *Attorney, Agent, or Firm* — Argus Intellectual Enterprise; Daniel Enea; Jordan Sworen

(57) ABSTRACT

A ultraviolet sanitation system including a towel assembly, a body configured to be an upward facing hollow-half-sphere and to contain a sanitizing liquid, a plate including two grooves, each of the grooves configured to accept a t-handle and a roller-ball of the towel assembly with the plate affixable to the body, and a plurality of wringing-rollers within the body beneath the plate configured to remove excess moisture from the towel assembly during use. Also include is an arm-assembly affixable to the base configured to restrain the plate, a sanitizing ultraviolet-light-source contained with the body below the plate, a base affixable to a bottom of the body, and a power-source electrically coupled to said ultraviolet-light-source.

13 Claims, 5 Drawing Sheets

ULTRAVIOLET SANITATIONS SYSTEM AND METHOD

BACKGROUND OF THE INVENTION

The following includes information that may be useful in understanding the present disclosure. It is not an admission that any of the information provided herein is prior art nor material to the presently described or claimed inventions, nor that any publication or document that is specifically or implicitly referenced is prior art.

TECHNICAL FIELD

The present invention relates generally to the field of drying and gas or vapor contact with solids of existing art and more specifically relates to a washer using ultraviolet energy.

RELATED ART

Generally speaking, a towel is a piece of absorbent fabric and/or paper used for drying or cleaning a surface or body, by wicking moisture through direct contact. In homes, hospitals, or other settings, several types of towels may be used, including hand towels, bath towels and/or kitchen towels. In warmer or sunny climates, individuals may also use beach towels. Paper towels are often provided in a commercial or office bathrooms for users to dry their hands. Paper towels are also used in households for a range of wiping, cleaning and drying tasks. Paper towels are disposable, providing significant waste, whereas cloth towels are generally reusable. One such limitation with cloth towels is that such towels must be washed and sanitized after each use.

Once such method of sanitization of cloth towels includes laundering. Laundering is the washing of cloth materials with water and a soapy solution. The laundry process is often done in a room reserved for that purpose; in an individual home this is referred to as a laundry room or utility room. An apartment building, hospital, or student hall of residence may have a shared laundry facility. A stand-alone business which launders may referred to as a laundromat. Such establishments can take up valuable space. Still, laundering cloth materials may not fully disinfect/sanitize cloth materials. Another method of sterilization includes ultraviolet irradiation as a disinfection method that uses short-wavelength ultraviolet light to kill or inactivate microorganisms such as bacteria.

The application of ultraviolet light to disinfect has been an accepted practice since the mid 20th century. Such methods have been used primarily in medical settings and sterile work facilities (e.g., clean-rooms, white-rooms, etc.). More recently such methods have been employed to sterilize drinking and wastewater. Still, there exists a need to fully disinfect cloths using a combination of available technology. Therefore a suitable solution is desired.

U.S. Pub. No. 2012/0056102 to Kenneth A. Stanley et al. relates to an ultraviolet light sanitizing method and apparatus. The described ultraviolet light sanitizing method and apparatus includes a unit, system, and method for disinfecting or sterilizing the entire surface area of an item. The system includes at least one ultraviolet light source producing ultraviolet light for disinfecting the item. In addition, the system includes a cavity housing the ultraviolet light source, the cavity having a reflective interior for redirecting light produced by the at least one ultraviolet light source. Furthermore, the system includes a shelf positioned above a bottom portion of the cavity to support the item, with the shelf capable of passing light produced by the at least one ultraviolet light source to disinfect a surface area of the item.

SUMMARY OF THE INVENTION

In view of the foregoing disadvantages inherent in the known washer art, the present disclosure provides a novel ultraviolet sanitation system and method. The general purpose of the present disclosure, which will be described subsequently in greater detail, is to provide an ultraviolet sanitation system and method for efficient use with towels, textiles, and/or garments.

An ultraviolet sanitation system is disclosed herein. The ultraviolet sanitation system includes a towel assembly, a body, a plate, a plurality of wringing-rollers, an arm-assembly affixable to the base configured to restrain the plate, an ultraviolet-light-source contained with the body below the plate, with the ultraviolet-light source configured to provide sanitation to the towel assembly during use, a base affixable to a bottom of the body, and a power-source. Also included are agitating bristles.

The towel assembly includes a fabric, a front-side, and a back-side, a t-handle affixed to one edge of the perimeter, and a roller-ball affixed to an edge-opposite (opposing) the t-handle. The fabric of the towel assembly includes a microfiber material. The body is configured to be an upward facing hollow-half-sphere and to contain a sanitizing liquid, and the plate includes a; the groove configured to accept the t-handle and the roller-ball with where the plate is affixable to the body.

The plurality of wringing-rollers are affixable and contained within the body beneath the plate configured to remove excess moisture from the towel assembly during use. Also, the arm-assembly is affixable to the base configured to restrain the plate.

The base is affixable to a bottom of the body, with the base including a plurality of wheels such that the system is readily movable by a user, and the base is also configured to be placeable upon a horizontal surface. The power-source is electrically coupled to the ultraviolet-light-source, with the power source including a 110/120 volt (i.e. household) electrical connection or the like.

According to another embodiment, a method of using an ultraviolet sanitation system is also disclosed herein. The method of use includes a first step, providing an ultraviolet sanitation system (the system including a towel assembly, a body, a plate, a plurality of wringing-rollers), an ultraviolet-light-source, a base, and power-source; a second step, providing a sanitizing liquid; a third step, placing the sanitizing liquid within the body of the system; a fourth step, inserting the towel-assembly into the system; a fifth step, sanitizing the towel-assembly via the ultraviolet-light-source and the sanitizing liquid; a sixth step, removing the towel-assembly from the system; and a seventh step, hanging the towel-assembly to dry.

For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and methods of use for the present disclosure, an ultraviolet sanitation system and method, constructed and operative according to the teachings of the present disclosure.

The various embodiments of the present invention will hereinafter be described in conjunction with the appended drawings, wherein like designations denote like elements.

DETAILED DESCRIPTION

Figure 1:
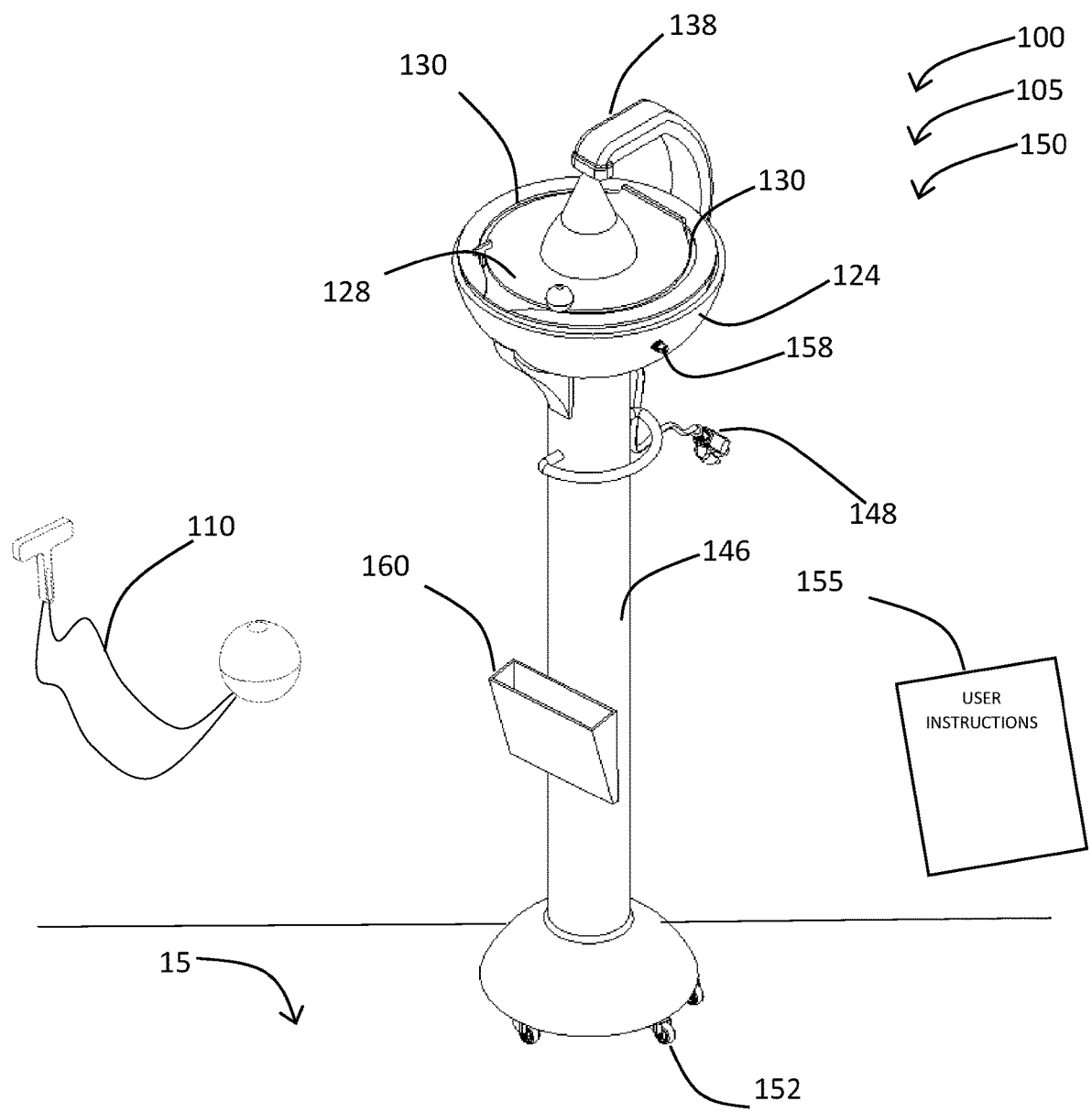
FIG. 1 is a perspective view of the ultraviolet sanitation system during an 'in-use' condition, according to an embodiment of the disclosure.
Figure 2:
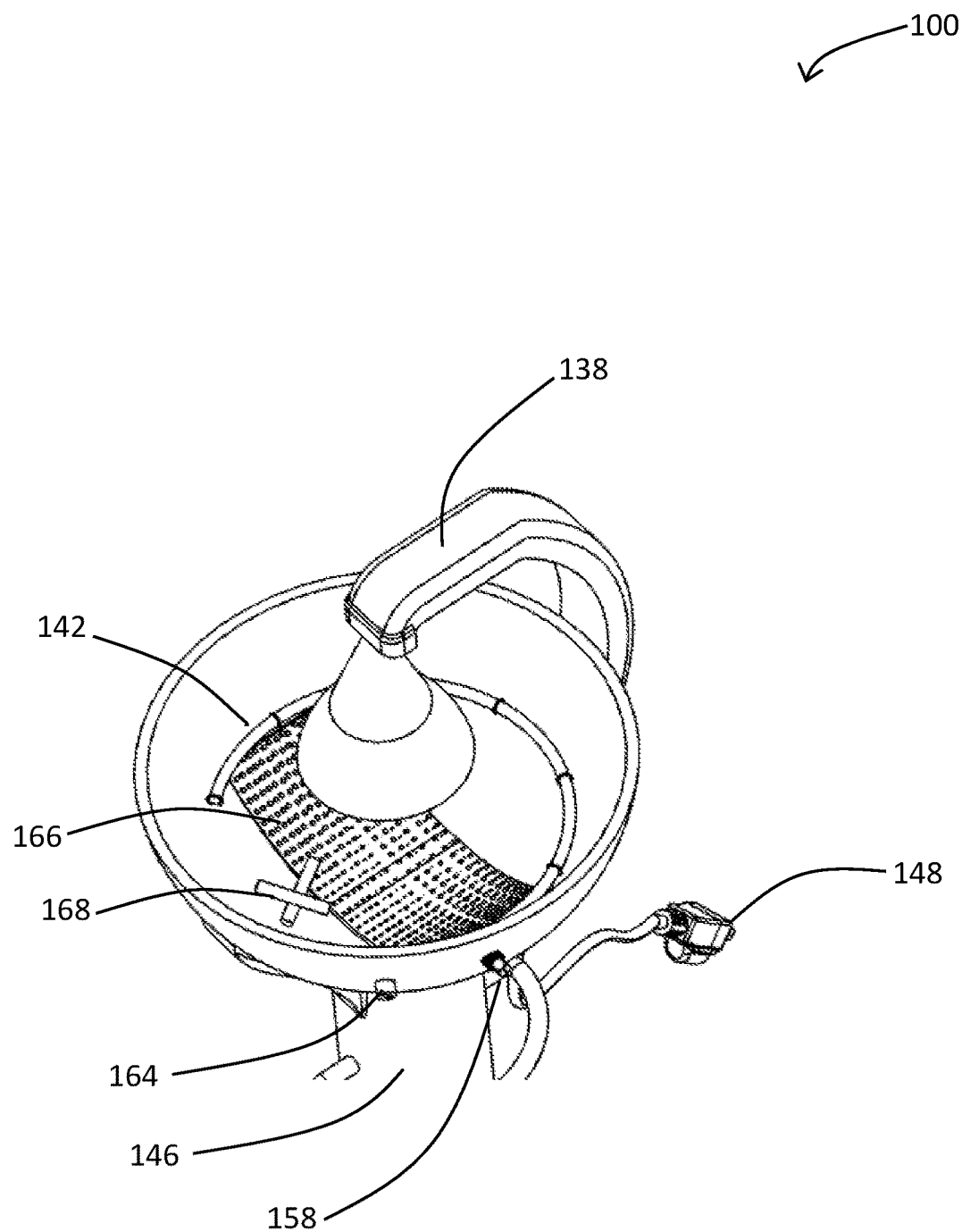
FIG. 2 is a perspective view of the ultraviolet sanitation system of FIG. 1, according to an embodiment of the present disclosure.
Figure 3:
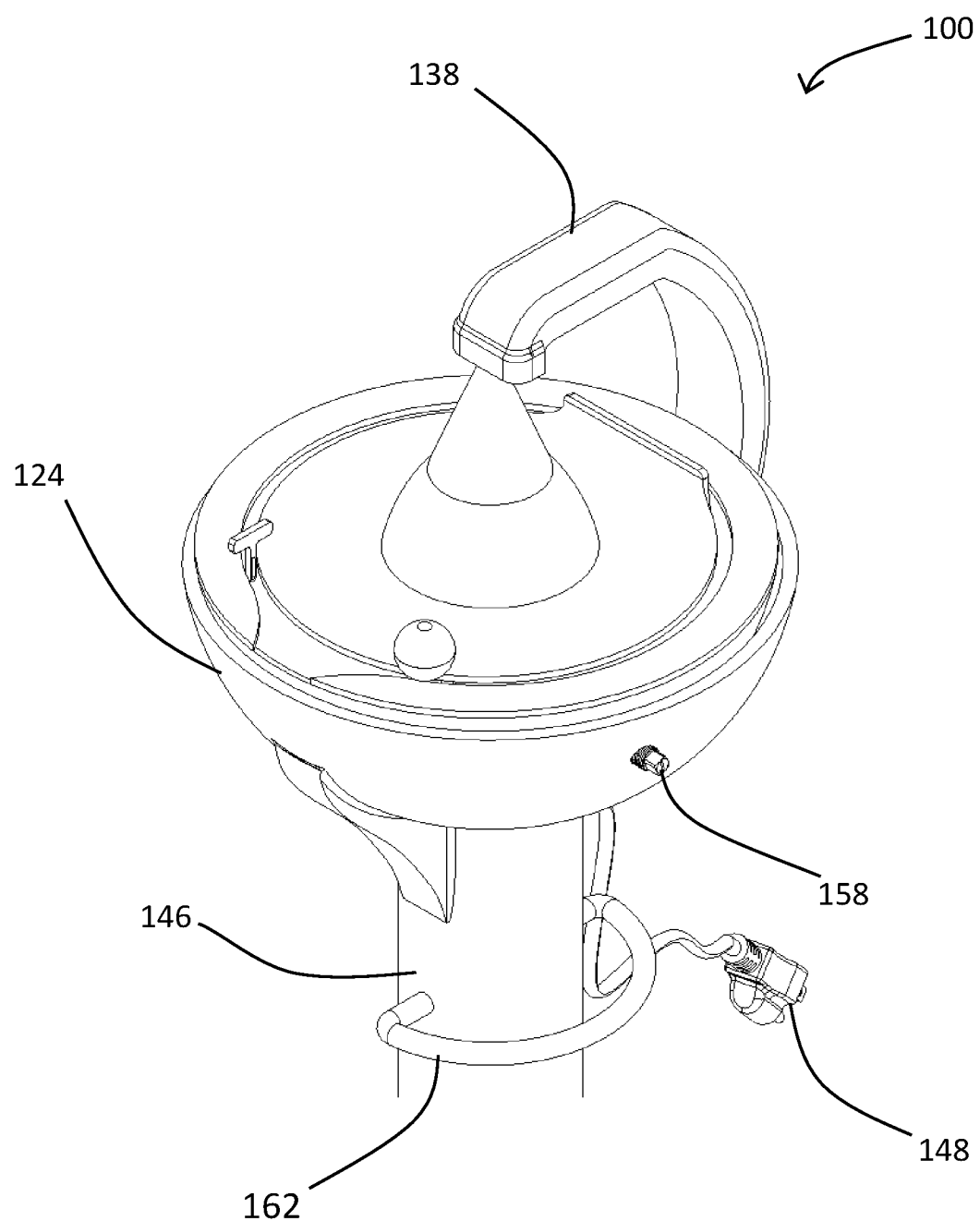
FIG. 3 is a perspective view of the ultraviolet sanitation system of FIG. 1, according to an embodiment of the present disclosure.
Figure 4:
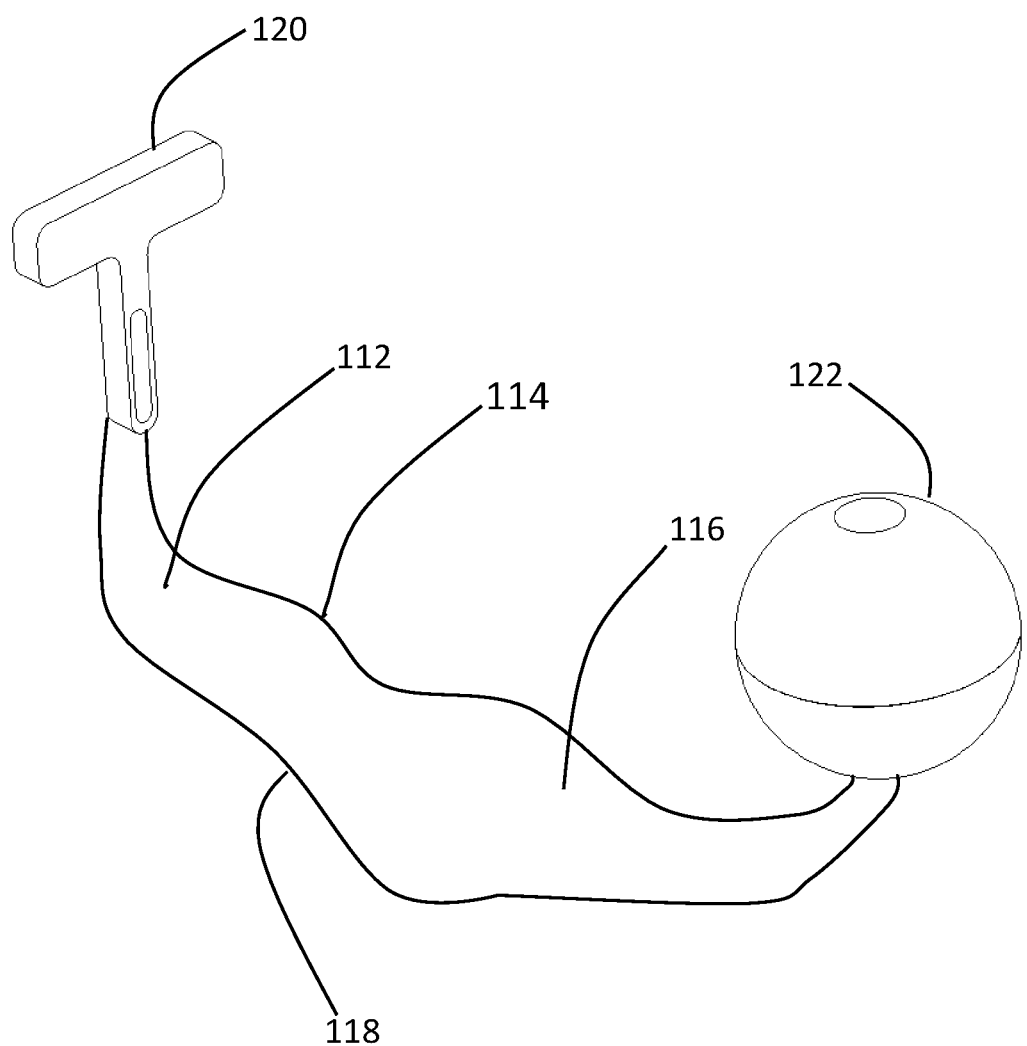
FIG. 4 is a perspective view of the ultraviolet sanitation system of FIG. 1, according to an embodiment of the present disclosure.

As discussed above, embodiments of the present disclosure relate to washing means and more particularly to an ultraviolet sanitation system and method as used to improve the cleaning and sterilization of fabric cloths.

Generally, the ultraviolet sanitation system includes a wall mount or self-standing device which allows reusable micro-fiber cloths to be cleaned and disinfected with ultraviolet light as well as a liquid solution by pulling the cloths through the device in one end and out of the other via a t-handle affixed to the cloth, therefore producing an outcome of a sanitized and 'wrung-out' cloth.

Referring now more specifically to the drawings by numerals of reference, there is shown in FIGS. 1-4, various views of an ultraviolet sanitation system 100.

FIGS. 1-4 show an ultraviolet sanitation system 100 during an 'in-use' condition 150, according to an embodiment of the present disclosure. Here, ultraviolet sanitation system 100 may be beneficial for use by a user to provide a device to clean and sanitize reusable cloths with minimal waste and effort. As illustrated, ultraviolet sanitation system 100 may include towel assembly 110, body 124, plate 128, plurality of wringing-rollers 168, arm-assembly 138, base 146, and power-source 148. Embodiments may also include bristles 166 to provide agitation during sanitation. Bristles 166 may include manual operation, in some embodiments. Embodiments may include bristles 166 that are mechanically operated (e.g., powered to rotate, shift, vibrate, etc.). Towel assembly 110 may include fabric 112; wherein fabric 112 may have perimeter 114, front-side 116, and back-side 118. Also included in towel assembly 110 may be t-handle 120 affixed to one edge of perimeter 114, and roller-ball 122 affixed to an edge-opposite t-handle 120. Fabric of towel assembly 110 may include a micro-fiber material. Also, t-handle 120 may be removable from towel assembly 110. Similarly, roller-ball 122 may be removable from towel assembly 110. Towel assembly 110 may comprise a wide variety of shapes (e.g., round, square, rectangular, triangular, etc.) and/or sizes (e.g., bath towels, hand-towels, dish towels, gym towels, etc.) depending upon the specific application and user preferences.

Body 124 may be configured to be an upward facing hollow-half-sphere, to contain a sanitizing liquid. Body 124 may further include drain-plug 158 configured to provide removal of the sanitizing liquid from body 124, in some embodiments.

Plate 128 of ultraviolet sanitizing system 100 may include a groove 130, where the groove 130 may be configured to accept t-handle 120 and roller-ball 122 of towel assembly 110, where plate 128 may be affixable to body 124. Embodiments may include plate 128 constructed from a transparent material. Also, plurality of wringing-rollers may be affixable, and contained within, body 124 beneath plate 128 and be configured to remove excess moisture from towel assembly 110 during use. Also included may be arm-assembly 138 affixable to base 146 configured to restrain plate 128.

Base 146 may be removably affixable to a bottom of body 124. Also, base 146 may be affixable to a vertical surface, in certain embodiments. Other embodiments may include base configured to be placeable upon horizontal surface 15. Embodiments may also include base 146 further including a plurality of wheels 152 such that system 100 is readily movable by a user.

Ultraviolet-light-source 142 may be contained within body 124 below plate 128, configured to provide sanitation to towel assembly 110 during use, operated by power-source 148. Power-source may 148 be electrically coupled to ultraviolet-light-source 142 and may include a 110/120 volt electrical connection. Embodiments may include power-source 148 including a battery. The battery may removable and replaceable, battery may also be rechargeable. Also, battery may be rechargeable via a 110/120 volt electrical connection where the battery need not be removed from the system for (re)charging.

In embodiments, system 100 may further include storage-compartment 160 to store a plurality of towel assemblies 110. Also, system 100 may further, or alternately, include drying-rack 162 configured to hang at least one towel assembly 110.

According to one embodiment, ultraviolet sanitation system 100 may be arranged as kit 105. In particular, ultraviolet sanitation system 100 may further include set of instructions 155. Instructions 155 may detail functional relationships in relation to the structure of ultraviolet sanitation system 100 such that the ultraviolet sanitation system 100 can be used, maintained, or the like, in a preferred manner.

Embodiments of ultraviolet sanitation system 100 may be hard-wired to a municipal or localized electrical system, in embodiments. Further embodiments may include ultraviolet sanitation system 100 that is plumbed to a municipal water source and/or sanitation system, and may include a filtration system.

Figure 5:
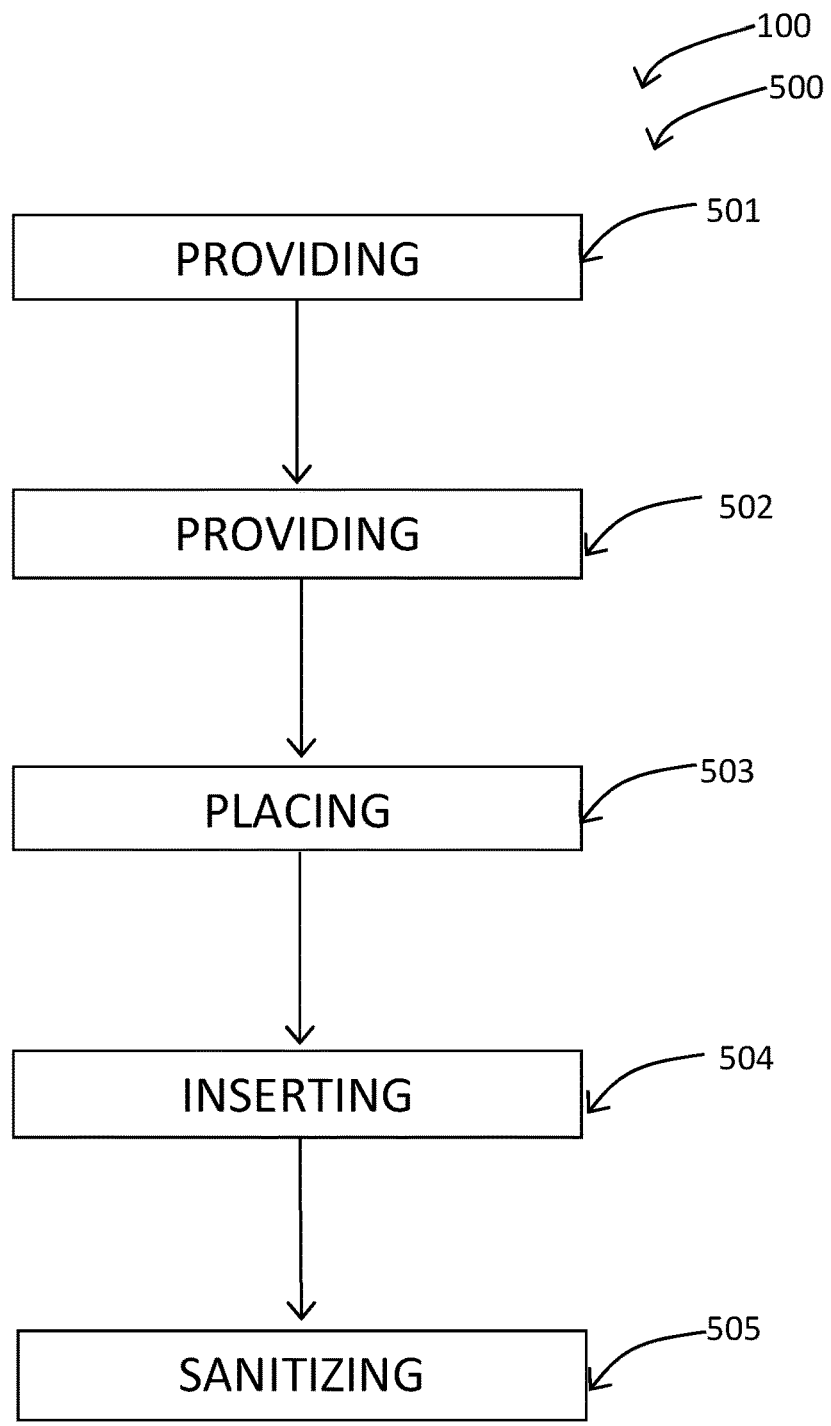
FIG. 5 is a flow diagram illustrating a method of using the ultraviolet sanitation system, according to an embodiment of the present disclosure.

FIG. 5 is a flow diagram illustrating a method of use 500 for an ultraviolet sanitation system 100, according to an embodiment of the present disclosure. In particular, the method of use 500 may include one or more components or features of ultraviolet sanitation system 100 as described above. As illustrated, the method of using 500 an ultraviolet sanitation system 100 may include the steps of: step one 501, providing an ultraviolet sanitation system 100 (system 100 including towel assembly 110, body 124, plate 128, and plurality of wringing-rollers 134), ultraviolet-light-source 142, base 146, and power-source 148; step two 502, providing a sanitizing liquid; step three 503, placing the sanitizing liquid within body 124 of system 100; step four 504, inserting towel-assembly 110 into system 100; step five 505, sanitizing towel-assembly 110 via ultraviolet-light-source 142, the sanitizing liquid, and/or mechanical or manual agitation as towel-assembly 110 is pulled through ultraviolet sanitation system 100; step six 506, removing towel-assembly 110 from system 100; and step seven 507, hanging towel-assembly 110 to dry.

It should be noted that step six 506 and step seven 507 are optional steps and may not be implemented in all cases. Optional steps of method of use 500 are illustrated using dotted lines in FIG. 5 so as to distinguish them from the other steps of method of use 500. It should also be noted that the steps described in the method of use can be carried out in many different orders according to user preference. The use of "step of" should not be interpreted as "step for", in the claims herein and is not intended to invoke the provisions of 35 U.S.C. § 112(f). It should also be noted that, under appropriate circumstances, considering such issues as design preference, user preferences, marketing preferences, cost, structural requirements, available materials, technological advances, etc., other methods of using an ultraviolet sanitation system 500 [NOTE: e.g., different step orders within above-mentioned list, elimination or addition of certain steps, including or excluding certain maintenance steps, etc.], are taught herein.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is new and desired to be protected by Letters Patent is set forth in the appended claims:

1. A method of sanitizing a towel, comprising:
   providing an ultraviolet sanitation system, the ultraviolet sanitation system comprising:
   a body having a plate removably secured to an open upper end of the body;
   a groove formed between the body and the plate, wherein the groove includes an open upper end extending around the open upper end of the body;
   wherein the groove is adapted to access an interior volume of the body and slidably receive a towel assembly;
   an ultraviolet light source adapted to emit ultraviolet light onto the towel assembly disposed within the body such that the ultraviolet light sanitizes the towel assembly;
   wherein the ultraviolet light source is operably connected to a power source adapted to provide electrical energy thereto;
   a sanitizing liquid disposed within the interior volume and adapted to saturate the towel assembly such that the sanitizing liquid light sanitizes the towel assembly;
   loading the towel assembly into the body, such that a handle of the towel assembly remains exterior the groove and provides for gripping of the handle;
   sliding the towel assembly from a first side of the groove to an opposing second side of the groove, such that the towel passes through the interior volume of the body;
   emitting the ultraviolet light onto the towel assembly disposed within the body such that the ultraviolet light sanitizes the towel assembly;
   removing the towel assembly from the ultraviolet sanitation system.

2. The method of claim 1, wherein the body of the ultraviolet sanitation system comprises an upward facing hollow-half-sphere.

3. The method of claim 2, the ultraviolet sanitation system further comprises a plurality of wring rollers, the plurality of wring rollers are arranged so as to move relative to each other and receive the towel assembly therebetween, wherein a wringing operation the plurality of wring rollers are adapted to compress the towel assembly to remove a portion of the sanitizing liquid from the towel assembly.

4. The method of claim 3, wherein the plurality of wringers comprises an upper wringer and a lower wringer.

5. The method of claim 1, wherein the ultraviolet sanitation system further comprises a single arm extending from an exterior side thereof at a first end and supporting the plate at a second end, wherein the arm removably supports the plate over the open end of the body such that the groove is continuous from the first side to the second side, thereby allowing the continuous sliding of the towel assembly within the groove from the first side to the second side.

6. The method of claim 5, wherein the ultraviolet sanitation system further comprises a drain-plug adapted to drain the interior volume of the sanitizing liquid.

7. The method of claim 5, wherein the ultraviolet sanitation system further comprises a stand having a wheel at a first end and the body at the second end thereof, wherein the stand is configured to maintain the ultraviolet sanitation system in an upright position and the wheel is adapted for rolling movement thereof.

8. The method of claim 5, wherein the body comprises a bristle adapted to agitate the towel assembly as it slides through the interior volume of the body.

9. The method of claim 5, the ultraviolet sanitation system further comprises a plurality of wring rollers, the plurality of wring rollers are arranged so as to move relative to each other and receive the towel assembly therebetween, wherein a wringing operation the plurality of wring rollers is adapted to compress the towel assembly to remove a portion of the sanitizing liquid from the towel assembly.

10. The method of claim 5, wherein the towel assembly further comprises a towel fabric having a first handle disposed at a first end and a second handle at a second end;
   wherein the groove forms a pair of elongated channels extending on opposing right and left sides thereof;
   wherein the first and second handle are sized to prevent entry into the groove when the towel fabric is positioned within the respective right and left channels and adapted for insertion into and through the groove.

11. The method of claim 10, wherein the first handle is a t-handle and the second handle is a roller-ball.

12. The method of claim 11, wherein the plate is constructed from a transparent material.

13. The method of claim 12, wherein the ultraviolet sanitation system includes a drying-rack configured to hang the towel assembly.

* * * * *